United States Patent [19]

Escher et al.

[11] Patent Number: 5,378,845
[45] Date of Patent: Jan. 3, 1995

[54] PROCESS FOR THE PRODUCTION OF 2-HALO-4,6-DIALKOXY PYRIMIDINES

[75] Inventors: André Escher, Glis; Felix Previdoli, Brig; René Imwinkelried, Brig-Glis, all of Switzerland

[73] Assignee: Lonza, Ltd., Basel, Switzerland

[21] Appl. No.: 101,761

[22] Filed: Aug. 4, 1993

[30] Foreign Application Priority Data

Aug. 5, 1992 [CH] Switzerland .......................... 2458/92

[51] Int. Cl.$^6$ ............................................. C07D 239/52
[52] U.S. Cl. ..................................................... 544/319
[58] Field of Search ............................................. 544/319

[56] References Cited

U.S. PATENT DOCUMENTS 3,225,077 12/1965 Schaefer et al. .................. 260/453

FOREIGN PATENT DOCUMENTS

| 0024200 | 2/1981 | European Pat. Off. |
| 0100425 | 2/1984 | European Pat. Off. |
| 0271834 | 6/1988 | European Pat. Off. |
| 0424849 | 5/1991 | European Pat. Off. |
| 0476554 | 3/1992 | European Pat. Off. |
| 2562070 | 10/1985 | France |
| 3939965 | 6/1991 | Germany |
| 3200784 | 2/1991 | Japan |

OTHER PUBLICATIONS

Chemical Abstracts, vol. 61, No. 5, (Aug. 1964), 6301h, Natsumoto et al.
Bee, J. A., and F. L. Rose, J. Chem. Soc., (1966), pp. 2031 to 2038.
McElvain and Schroeder, J. Am. Chem. Soc., 71, (1949), pp. 40 to 53.

*Primary Examiner*—John M. Ford
*Attorney, Agent, or Firm*—Fisher, Christen & Sabol

[57] ABSTRACT

A process for the production of 2-halo-4,6-dialkoxypyrimidines of the general formula:

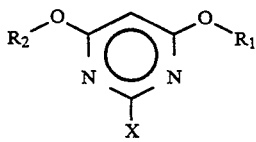

I starting from a propanediimidate or its salts. In the first stage, a propanediimidate or its salts of the general formula:

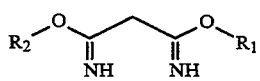

II is/are converted with cyanamide of the formula:

H$_2$N—CN   III in the presence of a base at a pH values above pH 7 into a cyanimidate of the general formula:

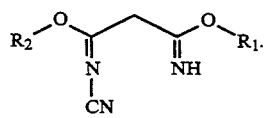

IV

The latter is then converted in the second stage with a hydrogen halide into the end product according to formula I.

15 Claims, No Drawings

PROCESS FOR THE PRODUCTION OF 2-HALO-4,6-DIALKOXY PYRIMIDINES

BACKGROUND OF THE INVENTION

1. Field of the Invention

The invention relates to a new process for the production of 2-halo-4,6-dialkoxy pyrimidines of the general formula:

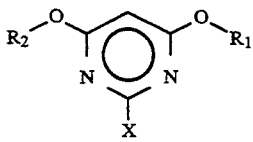

wherein X is a halogen atom, and $R_1$ and $R_2$ are the same or different and each is a $C_1$–$C_4$-alkyl group, starting from a propanediimidate and/or at least one of its salts.

2. Background Art

A known embodiment (process) for the production of a 2-halo-4,6-dialkoxypyrimidine derivative is described by J. A. Bee and F. L. Rose, J. Chem. Soc., (1966), pages 2031 to 2038. In such process the 2-halo-4,6-dialkoxypyrimidine derivative 2-chloro-4,6-dimethoxypyrimidine is synthesized by diazotization of 2-amino-4,6-dimethoxypyrimidine with sodium nitrite and subsequently hydrolysis with concentrated hydrochloric acid. A serious drawback of such process is that the 2-chloro-4,6-dimethoxypyrimidine is obtained in very poor yields.

BROAD DESCRIPTION OF THE INVENTION

The main objectives of the invention are to provide a process which eliminates the above-mentioned drawback of the prior art process and to provide a simple and economical process for the production of 2-halo-4,6-dialkoxypyrimidine derivatives wherein the product is obtained in good yields. Other objectives and advantages of the process are set out herein or are obvious herefrom to one skilled in the art.

The objectives and advantages of the invention are achieved by the process of the invention.

The invention involves a process for the production of 2-halo-4,6-dialkoxy-pyrimidines of the general formula:

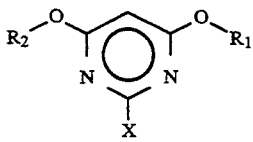

wherein X is a halogen atom, and $R_1$ and $R_2$ are the same or different and each is a $C_1$–$C_4$-alkyl group.

According to the invention the process is carried out so that, in the first stage, a propanediimidate and/or at least one of its salts of the general formula:

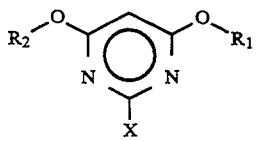

wherein $R_1$ and $R_2$ have the above-mentioned meaning is converted with cyanamide of the formula:

$$H_2N-CN \qquad III$$

in the presence of a base at a pH value above pH 7 into a cyanimidate of the general formula:

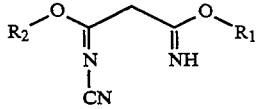

wherein $R_1$ and $R_2$ have the above-mentioned meaning, and the cyanimidate of formula IV is then converted in the second stage with a hydrogen halide into the end product according to general formula I.

2-Halo-4,6-dialkoxypyrimidines are, for example, important intermediate products for the production of 2-phenoxypyrimidine derivates having herbicidal effect (Japanese Published Patent Application No. 03-200784).

DETAILED DESCRIPTION OF THE INVENTION

The feedstocks of the process according to the invention, that is, propanediimidates (general formula II) or their salts, can be produced according to known methods starting from malonic acid dinitrile (McElvain and Schroeder, J. Am. Chem. Soc., 71, (1949), pages 40 to 53). The suitable radicals $R_1$ and $R_2$, which can be the same or different, of the propanediimidates, are a methyl, ethyl, propyl or butyl group. Preferably 1,3-dimethylpropanediimidate ($R_1=R_2$=a methyl group) is used as the propanediimidate.

Suitably the first stage of the process according to the invention is carried out so that the propanediimidate or its salts is/are added to a solution of base and cyanamide (formula III) and specifically so that the pH is adjusted to above pH 7. As salts of the propanediimidates, monohydrohalide or dihydrohalide salts, such as, the salts of hydrofluoric, hydrochloric or hydrobromic acid, can be used. Preferably dihydrochloride salt is used.

Alkali or alkaline earth bicarbonates, carbonates, hydroxides or alcoholates, for example, can be used as the bases.

Preferably an alkali bicarbonate, such as, sodium or potassium bicarbonate, especially potassium bicarbonate, is used as the base suitably the base is used either equimolar or in slight excess relative to the propanediimidate. Preferably the base is used in an amount of 1 to 1.1 mol per mol of the propanediimidate.

The cyanamide can be used equimolar or also in slight excess relative to the propanediimidate. Preferably the cyanamide is used in an amount of 1 to 1.5 mol per mol of the propanediimidate.

Suitably the reaction in the first stage is carried out at a pH of 7 to 12, preferably of 7 to 9. The reaction in the first stage is suitably carried out at a temperature of $-25°$ to $150°$ C., preferably of $0°$ to $50°$ C.

Suitable solvents for the first stage are, for example: water; ketones, such as, acetone or methylisobutylketone; alcohols, such as, methanol or ethanol; hydrocarbons, such as, toluene or xylene; halogenated hydrocarbons, such as, dichloromethane or 1,2-dichloroethane; and esters, such as, methyl acetate or ethyl acetate. Also mixtures of these solvents can be used. Preferably water is used as the solvent.

After a usual reaction time of 1 to 10 hours, the cyanimidate of general formula IV can then be isolated in a manner usual to one skilled in the art.

In the second stage the cyanimidate of general formula IV is converted with a hydrogen halide into the end product according to formula I.

As the hydrogen halide, hydrochloric acid, hydrobromic acid or hydroiodic acid, can be used. Preferably hydrochloric acid or hydrobromic acid is used. The hydrogen halide can be used in an amount of 2 to 20 mol per mol of cyanimidate. Preferably the hydrogen halide is introduced gaseous form up to the saturation level into the reaction vessel.

The temperature in the second stage is suitably between $-50°$ and $50°$ C., preferably between $-20°$ and $10°$ C.

Suitable solvents for the second stage are inert organic solvents, such as, tetrahydrofuran, toluene, acetonitrile, methylene chloride or low-boiling alcohols. Preferably tetrahydrofuran or toluene is used.

After a usual reaction time of 1 to 10 hours, the 2-halo-4,6-dialkoxy-pyrimidine of general formula I is isolated according to methods usual to one skilled in the art.

EXAMPLE 1

Production of 2-chloro-4,6-dimethylpyrimidine 10 g of potassium bicarbonate is dissolved in 50 ml of water and cooled to 0° C. Then 5.58 g of cyanamide was added. The pH was at 8.3. Then 20.3 g of dimethyl-propanediimidate-dihydrochloride was added under $CO_2$ generation at 0° C. for about 7 minutes. After ending the addition, the reaction solution was heated to room temperature and a solid precipitated from the yellowish, clear solution. After 4 hours at room temperature the precipitated solid was filtered by suction and washed with 20 ml. of water. Drying of the filter residue in a vacuum at 20° C. for 2 days yielded 11.17 g of 3-amino-3-methoxy-N-cyano-2-propenimidate as white solid, which was suspended under a $N_2$-stream in 50 ml of tetrahydrofuran and cooled to $-20°$ C. The suspension was saturated at $-20°$ to $-15°$ C. with a total 40 g of HCl gas. After 5 hours of HCl introduction, the reaction mixture was heated to 5° to 10° C. and completely concentrated by evaporation on a rotary evaporator. The residue after concentration by evaporation, was taken up in 50 ml of water, stirred and filtered by suction. The filter residue was washed free of chloride 3 times with 50 ml of water and dried overnight in a vacuum at 35° C. 10.12 g of 2-chloro-4,6-dimethoxypyrimidine was obtained as white crystals (GC 98.4%), corresponding to a yield of 57 percent relative to the dimethylpropanediimidate-dihydrochloride used.

EXAMPLE 2

Production of 2-bromo-4,6-dimethoxypyrimidine

The production of 3-amino-3-methoxy-N-cyano-2-propenimidate (first stage) was carried out analogously to Example 1. 5 g of 3-amino-3-methoxy-N-cyano-2-propenimidate was introduced in 50 ml of toluene. The suspension was cooled to $-5°$ C. Then HBr-gas was introduced in the reaction suspension at this temperature for 3 hours. For working up, the mixture was concentrated by evaporation on a rotary evaporator, and the residue was taken up in ethyl acetate and washed with water. The organic phase was dried on $Na_2SO_4$ and concentrated by evaporation. 0.67 g of product was obtained.

What is claimed is:

1. A process for the production of a 2-halo-4,6-dialkoxypyrimidine of formula:

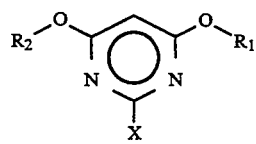

wherein X is a halogen atom, and $R_1$ and $R_2$ are the same or different and each is a $C_1$–$C_4$-alkyl group, comprising: in a stage, converting a propanediimidate or at least one salt thereof of formula:

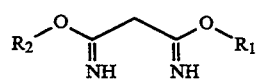

wherein $R_1$ and $R_2$ have the above-mentioned meaning, with a cyanamide of formula:

in the presence of a base at a pH value above pH 7 into a cyanimidate of formula:

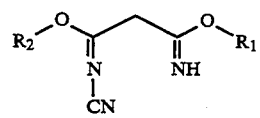

wherein $R_1$ and $R_2$ have the above-mentioned meaning, and, in a second stage, converting the cyanimidate of formula IV with a hydrogen halide into the 2-halo-4,6-dialkoxypyrimidine of formula I.

2. The process according to claim 1 wherein, in the first stage, the propanediimidate is at least one member selected from the group consisting of 1,3-dimethyl-propanediimidate and at least one salt thereof.

3. The process according to claim 2 wherein an alkali bicarbonate is used as the base in the first stage.

4. The process according to claim 3 wherein the reaction in the first stage is carried out at a pH of 7 above to 12.

5. The process according to claim 4 wherein the reaction in the first stage is carried out at a temperature of $-25°$ to 150° C.

6. The process according to claim 5 wherein hydrochloric acid or hydrobromic acid is used as the hydrogen halide in the second stage.

7. The process according to claim 6 wherein the reaction in the second stage is carried out at a temperature of $-50°$ to 50° C.

8. The process according to claim 1 wherein an alkali bicarbonate is used as the base in the first stage.

9. The process according to claim 1 wherein the reaction in the first stage is carried out at a pH of 7 above to 12.

10. The process according to claim 1 wherein the reaction in the first stage is carried out at a temperature of $-25°$ to 150° C.

11. The process according to claim 1 wherein hydrochloric acid or hydrobromic acid is used as the hydrogen halide in the second stage.

12. The process according to claim 1 wherein the reaction in the second stage is carried out at a temperature of −50° to 50° C.

13. The process as claimed in claim 1 wherein, in the first stage, the propanediimidate of formula II is used.

14. The process as claimed in claim 1 wherein, in the first stage, a monohydrohalide salt of the propanediimidate of formula II is used.

15. The process as claimed in claim 1 wherein, in the first stage, a dihydrohalide salt of the propanediimidate of formula II is used.

* * * * *